(12) United States Patent
Casper et al.

(10) Patent No.: US 6,716,883 B1
(45) Date of Patent: Apr. 6, 2004

(54) COMPOSITION USEFUL TO TREAT PERIODONTAL DISEASE

(75) Inventors: Robert F. Casper, Toronto (CA); Howard Charles Tenenbaum, Thornhill (CA)

(73) Assignee: 1333366 Ontario Inc., Toronto (CA)

( * ) Notice: Subject to any disclaimer, the term of this patent is extended or adjusted under 35 U.S.C. 154(b) by 0 days.

(21) Appl. No.: 09/868,451

(22) PCT Filed: Dec. 23, 1999

(86) PCT No.: PCT/CA99/01243

§ 371 (c)(1),
(2), (4) Date: Jun. 18, 2001

(87) PCT Pub. No.: WO00/38620

PCT Pub. Date: Jul. 6, 2000

Related U.S. Application Data

(60) Provisional application No. 60/113,937, filed on Dec. 24, 1998.

(51) Int. Cl.[7] ............................................. A61K 31/05
(52) U.S. Cl. .................................................... 514/733
(58) Field of Search ................................ 514/733, 734, 514/736; 424/48–58, 440

(56) References Cited

U.S. PATENT DOCUMENTS

| | | | |
|---|---|---|---|
| 6,008,260 A | | 12/1999 | Pezzuto et al. |
| 6,319,523 B1 | * | 11/2001 | Zhou .......................... 424/725 |
| 6,355,692 B2 | * | 3/2002 | Docherty ..................... 514/733 |
| 6,414,037 B1 | * | 7/2002 | Pezzuto ....................... 514/733 |
| 6,479,466 B1 | * | 11/2002 | Redfield et al. ............... 514/45 |
| 6,486,203 B1 | * | 11/2002 | Dannenberg ................. 514/473 |

FOREIGN PATENT DOCUMENTS

| | | |
|---|---|---|
| EP | 0 773 020 A | 5/1997 |
| FR | 2 766 176 A | 1/1999 |
| FR | 2 778 337 A | 11/1999 |
| WO | WO 98 33494 A | 8/1998 |
| WO | PCT/FR99/01063 | 11/1999 |
| WO | WO 99 59561 A | 11/1999 |

OTHER PUBLICATIONS

Aryl Hydrocarbon–Mediated Inhibition of Osteogenesis: Reversal by Resveratrol, A Novel Aryl Hydrocarbon Receptor Antagonist—Sacha U.N. Singh, 1999.

Resveratrol Has Antagonist Activity on the Aryl Hydrocarbon Receptor: Implications for Prevention of Dioxin Toxicity—Robert F. Casper, Monique Quesne, Ian M. Rogers, Takuhiko Shirota, Andre Jolivet, Edwin Milgrom, Jean–Francois Savouret—The American Society for Pharmacology and Experimental Therapeutics, 1999.

Ciolino et al: "Resveratrol inhibits transcription of CYP1A1 in vitro by preventing activation of the aryl hydrocarbon receptor", Cancer Research, US, American Association for Cancer Research, Vol 28, No. 24, Dec. 15, 1998 pp. 5707–5712; XP002090260 ISSN: 0008–5472, p. 5707.

Database WPI, Week 199729, Derwent Publications Ltd., London, GB; An 1997–311392; XP002140688 & CN 1 104 896 A (Chen), Jul. 12, 1995.

EPODOC abstract of CN1154850 (fang genfa), Jul. 23, 1997, XP002140687 abstract.

Subbaramaiah, Kotha et al: "Resveratrol inhibits the expresson of cyclooxygenase–2 in human mammary and oral apithelial cells"; Pharmaceutical Biology, (Dec. 1998) vol. 36, No. Suppl, pp. 35–43, XP000910993 whole document.

* cited by examiner

Primary Examiner—Shep K. Rose

(57) ABSTRACT

A composition and method for treating periodontal disease is provided comprising resveratrol in combination with a pharmaceutically acceptable carrier. The composition is particularly useful for administration to individuals at high risk of developing periodontal disease such as those who smoke tobacco products and those exposed to second-hand tobacco smoke or environmental pollutant AhR ligands.

25 Claims, 16 Drawing Sheets

1a Control
1b TCDD alone
1c Resveratrol alone
1d TCDD + resveratrol

R    T    TR    C

AP

BSP

Collagen

OPN

β-actin

COMPOSITION USEFUL TO TREAT PERIODONTAL DISEASE

This application claims the benefit of U.S. provisional application Ser. No. 60/113,937, filed Dec. 24, 1998.

FIELD OF THE INVENTION

The present invention relates to a composition useful to treat periodontal disease. In particular, the present invention relates to a composition comprising resveratrol, and its use to treat periodontal disease. It is particularly useful in the treatment of individuals at high risk for developing periodontal disease, for example, those exposed to high levels of aryl hydrocarbons such as individuals that smoke tobacco products, individuals exposed to second-hand tobacco smoke and individuals exposed to environmental pollutant AhR ligands.

BACKGROUND OF THE INVENTION

Periodontal disease is characterized by gingival inflammation, bone loss and loss of teeth. It is believed to be the most common cause of tooth loss resulting in significant dental morbidity.

Smokers are 2.5–6 times more likely to develop periodontal disease than non-smokers, and there is evidence for a direct correlation between the number of cigarettes smoked and the risk of developing the disease (Barbour et al, 1977, *Crit Rev Oral Biol Med* 8(4): 437–60). Smokers also tend to exhibit increased severity of periodontal disease compared to non-smokers with direct correlations between smoking and increased attachment loss, increased pocket depth, and reduced bone crest height (Barbour et al, supra). In addition, there is a strong association between smoking and both attachment loss and gum recession in young smokers (Linden et al, 1994, *J Periodontol* 65(7): 718–23) and even in subjects who have minimal or no periodontal disease (Gunsolley et al, 1998, *J Periodontol* 69(2): 165–70).

At the present time, it is not known how cigarette smoke exerts its negative effects on bone formation or bone-related diseases such as osteoporosis and periodontitis (Genco et al. J Int Acad Periodontol. 1999 1(1):21–33).

Proinflammatory cytokines such as tumor necrosis factor-alpha (TNF-$\alpha$) and interleukin 1$\beta$ (IL-1$\beta$) possess bone-resorptive properties, and are generally considered to play a role in the pathogenesis of periodontal disease (Hou et al, 1995, *J Clin Periodontol* 22(2): 162–7; Liu et al, 1996, *Cytokine* 8(2): 161–7; Galbraith et al, 1997, *J Periodontol* 68(9): 832–8). Pathogenic oral bacteria have been shown to cleave active IL-1$\beta$ from pro-IL-1$\beta$ (Beausejour et al, 1997, *Infect Immun* 65(8): 3199–202). Blocking antibodies, which inhibit IL-1/TNF, reduce both inflammatory cell recruitment and bone loss in patients with periodontal disease (Assuma et al, 1998, *J Immunol* 160(1): 403–9).

It has been demonstrated previously that aryl hydrocarbon receptor (AhR) ligands such as dioxin and benzo[a]pyrene, which are present in high concentrations in cigarette smoke, are powerful stimulators of IL-1$\beta$ and TNF-$\alpha$ and, thus, may be significant in the pathogenesis of periodontal disease in smokers. In this regard, AhR antagonists may be useful to block stimulation of IL-1$\beta$ and TNF-$\alpha$, thereby minimizing some symptoms of periodontal disease.

Resveratrol, the parent compound of a family of molecules including glucosides and polymers, is a potent AhR antagonist as described in French Patent Application No. 9805673 filed May 5, 1998. It is an anti-fungal agent or phytoalexin produced by plants classified as spermatophytes of which vines, peanuts and pines are prime representatives (Soleas et al., 1997, Clin Biochemistry, 30:91–113). As an AhR antagonist, resveratrol, the chemical name of which is 3,5,4'-trihydroxystilbene, is useful generally to prevent the toxic effects of environmental exposure to AhR ligands, including, for example, halogenated and polycyclic aryl hydrocarbons, polyaromatic hydrocarbons and polychlorinated biphenyls. In addition, resveratrol has been demonstrated to prevent the induction of the proinflammatory cytokine, IL-1 Beta, by AhR ligands (Casper et al. 1999. Molecular Pharmacology, 56:784–790).

Although there are many treatments for various aspects of periodontal disease, there remains a need to develop a method which focuses more directly on prevention of bone loss and loss of tooth attachment, particularly among patients who smoke tobacco products.

SUMMARY OF THE INVENTION

Accordingly, in one aspect, the present invention provides a composition for treating periodontal disease comprising resveratrol and a pharmaceutically acceptable carrier.

A method for treating periodontal disease in a patient is also provided comprising the step of administering a composition comprising resveratrol as described to the oral cavity of the patient.

In a further aspect of the present invention, there is provided an article of manufacture comprising packaging material and a pharmaceutical composition contained within said packaging material, wherein the composition comprises resveratrol in combination with at least one pharmaceutically acceptable carrier and is effective to treat periodontal disease, and the packaging material comprises a label which indicates that the composition is for use to treat periodontal disease.

Other aspects of the invention include the use of resveratrol for treating periodontal disease and for the manufacture of pharmaceutical compositions for treating periodontal disease.

These, and other aspects of the present invention, will be further described by reference to the following drawings in which:

DETAILED DESCRIPTION OF THE INVENTION

Figure 1:
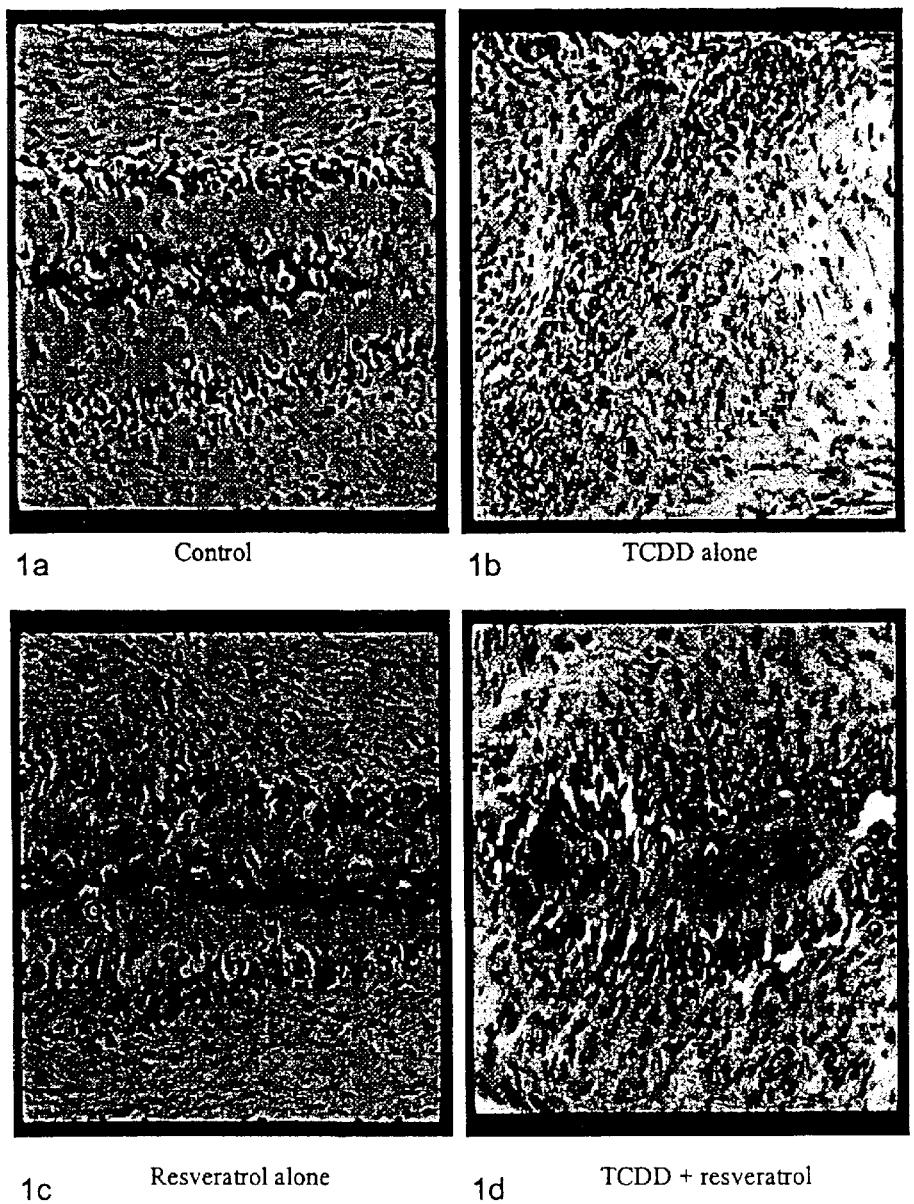
FIGS. 1A–D illustrate a histological evaluation of 5 $\mu$m thick paraffin-embedded sections obtained from chick periosteal osteogenesis (CPO) cultures including control (A), TCDD-treated (B), resveratrol-treated (C) and TCDD- and resveratrol-treated cultures (D)

A novel composition to treat periodontal disease is provided comprising resveratrol and a pharmaceutically acceptable carrier.

The term "treat" as it is used herein with respect to periodontal disease is meant to encompass both treatment of existing periodontal disease as well as prevention of anticipated periodontal disease. In this regard, prevention and treatment of periodontal disease in accordance with the present invention refers to the inhibition of, or at least the reduction of, inflammation, bone loss and/or attachment loss associated with periodontal disease.

The present composition comprises resveratrol. The term "resveratrol" is meant to encompass not only the parent compound, i.e. 3,5,4'-trihydroxystilbene, but also derivatives of resveratrol which are aryl hydrocarbon receptor (AhR) antagonists. Examples of resveratrol derivatives which are AhR antagonists include, but are not limited to, piceatannol (3,4,3',5'-tetrahydroxystilbene), oxyresveratrol (2,3',4,5'-tetrahydroxystilbene), 4,4'-dihydroxystilbene, and the alpha- and beta-glucoside, galactoside and mannoside derivatives thereof, such as piceid.

The present composition comprises resveratrol together with a pharmaceutically acceptable carrier. In this context, the term "pharmaceutically acceptable" means acceptable for use in the pharmaceutical and veterinary arts, i.e. a carrier which is non-toxic and which does not adversely affect the activity of resveratrol to treat periodontal disease. Pharmaceutically acceptable carriers useful to prepare the present composition for administration include conventional carriers used in formulating alcohol-soluble drugs, such as diluents, excipients and the like. Reference may be made to "Remington's Pharmaceutical Sciences", 17th Ed., Mack Publishing Company, Easton, Pa., 1985, for guidance on drug formulations generally. As will be appreciated, the pharmaceutical carriers used to prepare compositions in accordance with the present invention will depend on the desired administrable form.

According to one embodiment of the invention, the most appropriate administrable form of the present composition is a topical dosage form that can be applied to affected areas of the oral cavity. Appropriate topical dosage forms include pastes, gels, rinses, sprays (aerosol or other), powders for reconstitution, tablets and gums.

As set out above, the carrier and other components of the composition will vary with the selected administrable dosage form. For example, for the preparation of the present composition into a rinse or spray, the resveratrol may first be admixed with an appropriate alcohol, i.e. an alcohol that is suitable for administrationto the oral cavity of a patient and non-toxic at the dosage administered. An example of an appropriate alcohol is, for example, ethyl alcohol, in an amount ranging from about 5% to about 30% by weight of the composition. In accordance with one commercially acceptable rinse formulation, the active ingredient(s) is admixed with an amount of alcohol of about 27% by weight of the total composition. Once admixed with an appropriate alcohol, the resveratrol solution may be admixed with further additives, as will be more fully described, in order to be suitable for administration. For the preparation of the present composition into a dosage form other than a solution, i.e. a paste, gel, powder or gum, the resveratrol must first be micronized, using conventional physical procedures well known in the art, prior to being admixed with appropriate carriers.

In the case of a paste, micronized resveratrol is combined with carriers conventionally used to formulate a paste, including thickening agents such as methylcellulose or hydroxypropyl methylcellulose, humectants and surfactants, as described in more detail in EP 568 160 and U.S. Pat. No. 5,496,541, the contents of which are incorporated herein by reference.

In the case of a gel, micronized resveratrol may be admixed with gel carriers such as gelatin, polyethylene glycol, guar gum or combinations thereof. Structurant compounds are also normally present in a gel, examples of which include polyoxyethylene-polyoxypropylenecopolymers. Such structurants are generally present in amounts ranging from about 18 to about 25% by weight of the composition.

Toothpaste or gel forms of the present composition may further comprise an abrasive. Examples of suitable abrasives include water-insoluble alkali or alkaline earth metal salts of metaphosphate, calcium carbonate, aluminate and silicate. The amount of such abrasive generally contained in a toothpaste or gel ranges from about 5 to about 80% by weight of the composition.

In order to prepare the present composition into a chewing gum, micronized resveratrol may be combined with conventionally used carriers including one or more natural or synthetic elastomers, optionally supplemented with one or more solvents, plasticizers or fillers. Natural elastomers suitable for use include substances of vegetable origin such as chicle, jelutong, gutta percha, guayule and crown gum. Examples of synthetic elastomers include butadiene-styrene copolymers, isobutylene-isoprenecopolymers, polyethylene, polyisobutylene, polyvinylacetateand combinations thereof. The elastomer generally comprises from about 14% to about 50% by weight of the composition. Solvent may additionally be added to soften the elastomer component. Suitable solvents include methyl, glycerol or pentaerythritol esters of rosins or modified rosins, such as hydrogenated, dimerized or polymerized rosins as well as terpene resins such as polyterpene. Specific examples of such solvents include pentaerythritol ester of wood rosin, glycerol ester of partially dimerized or polymerized rosin, glycerol ester of tall oil rosin or wood rosin, and partially hydrogenated methyl ester of rosin. Such solvents may be used in an amount ranging from about 10% to about 75% of the composition. Resveratrol may be dissolved in such solvents or micronized and suspended in the solvent or elastomer phase of the preparation. Plasticizers, softeners or emulsifiers may also be included in the gum composition in an amount of up to about 30% by weight of the composition. Examples of these components include lanolin, lecithin, glyceryl monostearate, stearic acid, sodium stearate, postassium stearate, glyceryl triacetate, triacetin and glycerin, as well as natural waxes, petroleum waxes, paraffin waxes and microcrystalline waxes to improve texture and consistency.

The present composition may also be formulated to include one or more additional active ingredients provided that any such additional active ingredient or ingredients do not impact adversely on the activity of the composition to treat periodontal disease. Additional active ingredients may include, for example, fluoride compounds such as sodium fluoride, potassium fluoride, calcium fluoride, mangnesium fluoride, stannous fluoride, stannous monofluorophosphate, sodium monofluorophosphate and copper fluoride; antibacterial agents such as chlorhexidine, triclosan, sanguinarine and cetylpyridinium salts; antitartar agents such as tetrapotassium or tetrasodium pyrophosphates; anti-inflammatory agents such as ketoprofen and benzymidine; de-odourizers; stain removers; and other ingredients that would be well-known by those of skill in the art.

Other additives may also be included in the present composition to enhance its appeal. For example, flavouring agents based on oils of spearmint and peppermint may be added to the composition to provide a desirable tasting composition. Other compounds which may be used to provide a composition with an appealing flavour include menthol, clove, wintergreen eucalyptus and aniseed. An amount of flavouring agent suitable for inclusion in the present composition may be in the range of about 0.1 to about 5% by weight of the total composition. Sweetening agents may also be added to the present composition. Examples of suitable sweetening agents include, but are not to be limited to, saccharin, sodium cyclamate, aspartame, xylitol and sucrose. Sweetening agents generally comprise about 0.1 to about 5% by weight of the total composition. Colorant such as titanium dioxide, antioxidants such as ascorbic acid or alpha-tocopherol, buffer to retain the pH at an acceptable value including as an example potassium phosphate, preservative such as potassium sorbate or calcium propionate, silicone and other synthetic or natural polymers may also be added to the present composition in amounts that would not have an adverse effect on the activity of the composition as would be appreciated by one of skill in the art. For further discussion and examples of additives that may be added to the present composition, reference may be made to U.S. Pat. Nos. 5,496,541, 5,585,110, 5,298,237 and 5,616,313, the contents of each of which is incorporated herein by reference.

For use in treating individuals with periodontal disease, a therapeutically effective amount of the present composition is administered to the oral cavity of the individual for a suitable period of time. The term "therapeutically effective amount" means an amount of resveratrol sufficient to treat periodontal disease without causing intolerable side effects. Precise dosages of the composition appropriate for use to treat an individual are established in appropriately controlled clinical trials. As will be appreciated, the appropriate dosage of the present composition will vary with the administrable form of the composition. For example, it is anticipated that an effective treatment regimen will involve the administration of a dosage in the range of at least about 1 mg/g up to about 20 mg/g of paste or gel, or up to an amount of resveratrol which is capable of being absorbed by the paste or gel while still being cost effective; a range of at least about 0.2 mg/stick of gum up to about 200 mg/stick of gum, or up to an amount of resveratrol which is capable of being absorbed by the gum carriers while still being cost effective; and a range of about 0.001–5 g/liter of liquid rinse or spray, a preferred dosage of which being represented by about 0.02 g of resveratrol/liter.

It is believed that, in order to be effective in treating periodontal disease, the present composition must be in contact with affected areas of the oral cavity for an acceptable period of time per use, and must be used at least 1 to 3 times daily. The treatment time will vary with the administrable form of the composition. For example, in the form of a rinse, the composition is preferably used for 30–60 seconds per use, 2–3 times daily; in the form of a gel or paste, the composition is preferably used for about 1–2 minutes, 2–3 times daily; and in the form of a gum, the composition can be used for a longer period of time than other dosage forms, generally for at least several minutes per stick of gum.

For use in treating periodontal disease, the present invention provides in another of its aspects an article of manufacture which includes packaging material contained within which is a pharmaceutically acceptable resveratrol composition that is effective to treat periodontal disease. The packaging material comprises a label which indicates that the composition can be used to treat periodontal disease.

Specific embodiments of the present invention will be described in more detail in the following specific examples which are not to be construed as limiting.

EXAMPLE 1

Determination of Dioxin-Induced Bone Loss and Effect of Reservatrol

In this experiment, the chick periosteal osteogenesis (CPO) model was used to determine if bone loss is induced by dioxin. The CPO model has been described in detail previously (Nijweide, Proc. Kon. Ned. Akad. Wet. 1975. C78:410–417) and was prepared for the purposes of this experiment as set out below.

Following sacrifice, two triangular calvarial explants were removed by cutting along the central suture, transversely along the posterior suture and laterally above the eye in 17-day-old embryonic chicks. The ectocranial periosteum (outer curved surface) was peeled off using forceps under microscopic magnification and folded so that the surface originally facing bone was in apposition to itself as described previously (Tenenbaum et al., Calcif Tissue Int. 34:76–79). The folded explant was then placed on a Millipore filter (HA 0.45 $\mu$m), which was transferred onto a stainless steel grid resting in the center well of an organ culture dish (Falcon Plastics, Lincoln Park, N.J., USA) that was filled with culture media to a level such that the culture was supported at the gas-liquid interface (~1.5 ml of media). Three cultures were placed in each dish which was then covered and incubated at 37° C. in a humidified atmosphere containing 5% $CO_2$ in air. Media changes occurred on days 2 and 4, and the medium was comprised of $BGJ_b$ medium (Fitton-Jackson Modification) with L-glutamine (Gibco, Grand Island, N.Y., USA) and supplemented with 2% antibiotic (10,000 units/ml Penicillin G sodium, 10,000 μg/ml Streptomycin sulfate in 0.85% saline) (Gibco), 10% fetal calf serum (Gibco), $10^{-7}$M dexamethasone (Sigma, St. Louis, Mo., USA), 10 mM β-glycerophosphate, and 300 μg/ml L-ascorbate (Gibco).

For the purposes of this investigation, the effects of a potent aryl hydrocarbon, TCDD (2,3,7,8-tetrachlorodibenzo-p-dioxin or dioxin) on the early events occurring during osteogenesis were determined. The CPO model traverses a number of phases of osteogenesis. Therefore, it was possible to design temporal or "window" experiments in order to determine the phases of osteogenesis that were sensitive to TCDD and/or resveratrol. CPO cultures were treated with TCDD $10^{-9}$M, resveratrol $10^{-6}$M±TCDD $10^{-9}$M, or vehicle. All cultures were maintained for the entire 6-day period. The compounds were administered over four different temporal phases, as outlined below in the time-line diagram: a) days 0–6; b) days 0–2; c) days 2–4 or d) days 4–6 (Note: all cultures were stopped at 6 days). Results were compared to e) vehicle alone over days 0–6.

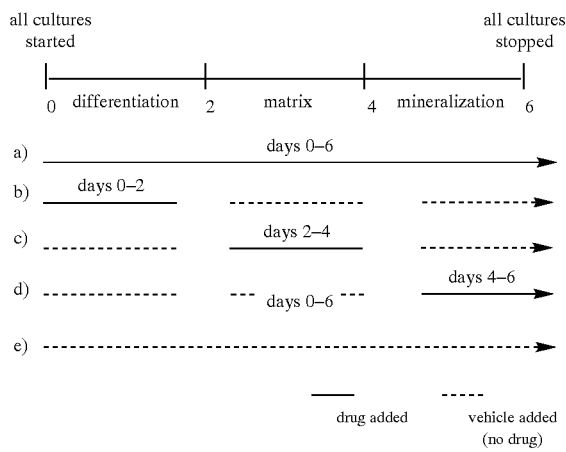

The cultures received vehicle control when not receiving resveratrol±TCDD and the media were changed every 48 hours. When given together, TCDD and resveratrol were added simultaneously to assess their effects in direct combination. On day 6, the culture dishes were placed on ice and individual cultures were transferred to separate test tubes and stored at −20° C. for further analysis.

As alkaline phosphatase activity (APA) has been shown to be a reliable marker of osteogenesis in this model system, it was chosen as a primary outcome measure (Tenenbaum et al., J. Histochem. Cytochem., 34:769–773, 1986b). CPO cultures were assayed for AP activity using paranitrophenol-phosphate (pN-p) as the substrate (Demetriou et al. J Biol Chem. 1996. 271(22)12755–61). The intensity of the colour change was evaluated using a Titertek® Multiskan® MCC/340 Spectrophotometer (Flow Laboratories, Mississauga, ON, Canada) and compared to a standard curve obtained from a serial dilution of 10 mM pN with bicarbonate buffer (pH 7.4) in flat bottomed Titertek 96-well plates as described previously (Demetriou et al., 1996, supra). The reaction was stopped with 100 μl of 0.2N NaOH and pN-p levels read at 405 nm on the Titertek. Calcium incorporation was assayed in the pellets produced from centrifugation of the homogenized CPO cultures following hydrolysis in 500 μl of 0.5N HCl and then measured using atomic absorption spectrophotometry (Sukhu et al. Endocrinology. 1997. 138 (8):3269–75).

The isolation of total RNA from periosteal cultures to determine affect of TCDD on message levels of bone proteins was accomplished using the QIAGEN Rneasy® kit and QIAShredder® (Hilden, Germany) according to the manufacturer's instructions. Total RNA (2 μg) was reverse transcribed using SuperScript II™ RNase H⁻ Reverse Transcriptase (Gibco BRL, City Country). PCR reactions were performed in 2 μl reactions at a cycle number ensuring a linear amplification profile (BSP, 5 min at 94° C., 30 cycles [of 20 sec at 94° C., 20 sec at 55° C., 20 sec at 72° C.]; Collagen 5 min at 94° C., 30 cycles [of 20 sec 94° C. 20 sec 58° C., 20 sec 72° C.]; AP 5 min at 94° C., 30 cycles [of 20 sec 94° C., 20 sec 59° C., 20 sec 72° C.]; OPN 5 min at 85° C., 5 min at 94° C., 25 cycles [20 sec at 94° C., 20 sec at 60° C., 20 sec at 72° C.] 7 min at 72° C.). The oligonucleotides for BSP (sense: 5'-GAGCGGGCACCGGTACTA-3'; antisense: 5'-CTCTAGACACTGACATCCTGCTC-3') AP (sense: 5'-ACCGCTGCAACACCACCA-3'; antisense: 5'-TCCCCGCAGGCTTAGTGT-3'), Collagen (sense: 5'-ACCCGACCCTAAGACAAA-3'; antisense: 5'-TCGGCGTTGGGGCAGT-3'); OPN (sense 5'-AGGCCGGGGTGACAGTGT-3'; antisense 5'-CCCCGCAGGCAGCACTC-3') were synthesized by Life Technologies (Gibco BRL, Rockville, Md.). PCR products were electrophoresed on 1.5 (wt/vol) % agarose gels with 0.1 μg/ml ethidium bromide. The gels were visualized on an UV transilluminator and photographed using 667 Polaroid film. The inverse images of the photographs were analyzed by densitometry. All values were normalized for the internal control, β-actin.

Radiolabeled collagen was measured in CPO cultures incubated with $^{14}$C-glycine (Amersham, 59 mCi/mMole) at a concentration of 10 μci/ml media in each group over days 4–6. The cultures were hydrolyzed in 0.1 ml of 0.1N HCl and vortexed. After 15 minutes, the supernatant was removed and saved in a 2 ml eppendorf tube. The culture was transferred to a 0.5 ml eppendorf tube containing 0.1 ml of pepsin (50 μg/ml in 0.1% glacial acetic acid) for further digestion of labeled collagen. These were maintained in a 15° C. water bath for 5 hours, vortexing the samples every hour. The supernatant was transferred to a new 0.5 ml eppendorf tube and was then lyophilized overnight. The amount of radiolabeled collagen was determined by gel electrophoresis as described hereunder. The lyophilized samples were reconstituted with 0.1 ml of a solution made of 70% sample buffer (10 mM Tris.HCl and 1 mM EDTA, pH 8.0) (Sigma-Aldrich Canada Ltd., Oakville, Canada), 2.5% SDS (Sigma), 5% β-mercaptoethanol (Sigma) and 0.01% bromophenol-blue (Sigma). The samples were boiled for 5 minutes and were loaded on a 7.5% homogenous SDS gel (Amersham Pharmacia Biotech, Inc, Quebec). The gel was then run on the PhastSystem® (Pharmacia, Quebec) at 250V, 10.0 mA, 3.0 W, 15° C. for 20 minutes.

Fluorography was used to analyze the amount of newly synthesized $^{14}$C-labeled collagen in each sample. Each gel was coated with 20% PPO in DMSO. The gels were then exposed to photographic film (Kodak, Rochester, N.Y., USA) for 2 days at −80° C., and the film then developed. The intensity of the resultant bands on the film was quantified using a laser densitometer to give a measure of the amount of newly synthesized collagen in each sample.

Results
Bone Formation in the CPO Model

As shown in FIGS. 1A–D, there were obvious changes in bone formation in CPO cultures treated with TCDD. Although morphometric measurements were not made, the TCDD-treated specimens (FIG. 1B) had to be sectioned completely to visualize any bone at all. In those cultures, however, the small amount of bone that did form appeared to be more or less normal in that there was recognizable bone matrix containing osteocytic cells that was also surrounded by osteoblast-like cells. There appeared to be a complete reversal of the TCDD effect in cultures treated with both TCDD and resveratrol (FIG. 1D). Large seams of bone were visualized readily and the bone, which was surrounded by a multilayer of osteoblasts (arrowhead), contained numerous osteocytes (small arrow). The bone seam and osteoblasts were surrounded by a collagen-rich layer of fibrous periosteum (f). The cultures treated with both TCDD and resveratrol were indistinguishable from control cultures (FIG. 1A) which contained easily recognizable seams of mineralized bone (M) surrounded by unmineralized osteoid (O). Cultures treated with resveratrol alone (FIG. 1C) also demonstrated large deposits of bone similar to the control cultures.

Biochemical Markers of Osteogenesis in CPO

Figure 2A:
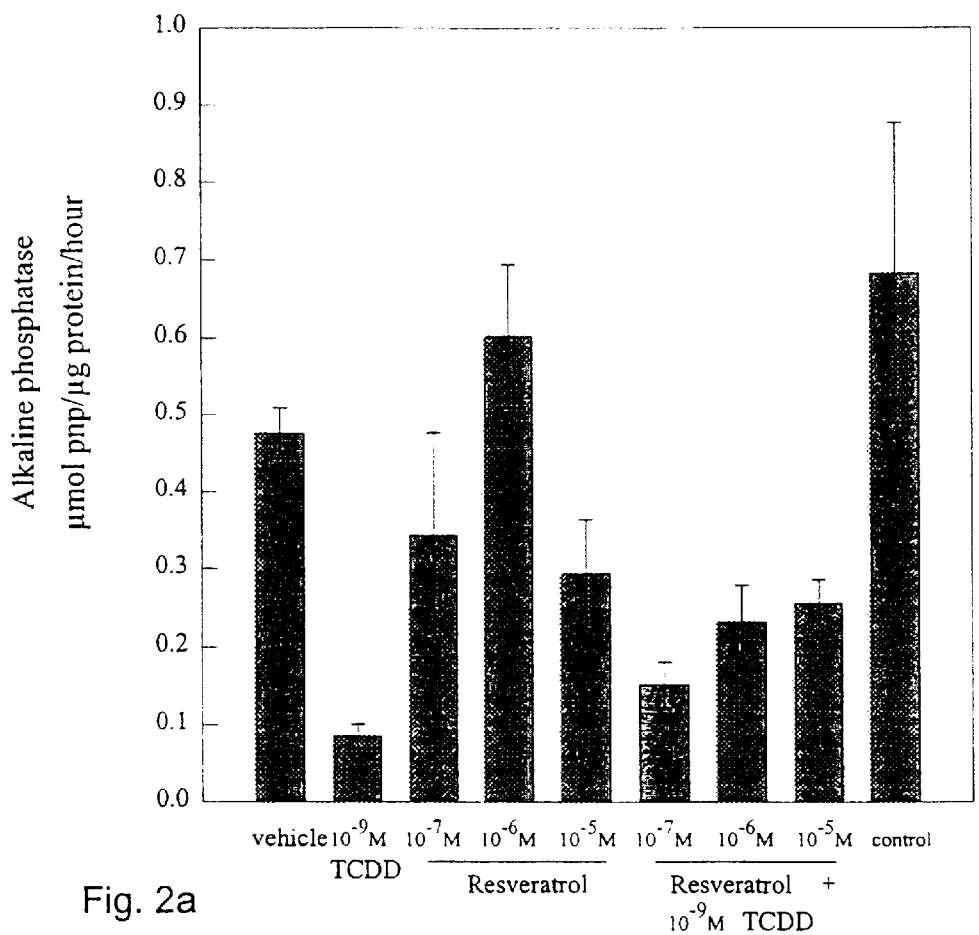
FIGS. 2A–C are bar graphs illustrating the effects of TCDD, reservatrol, and TCDD combined with resveratrol on APA in the CPO model.
Figure 2B:
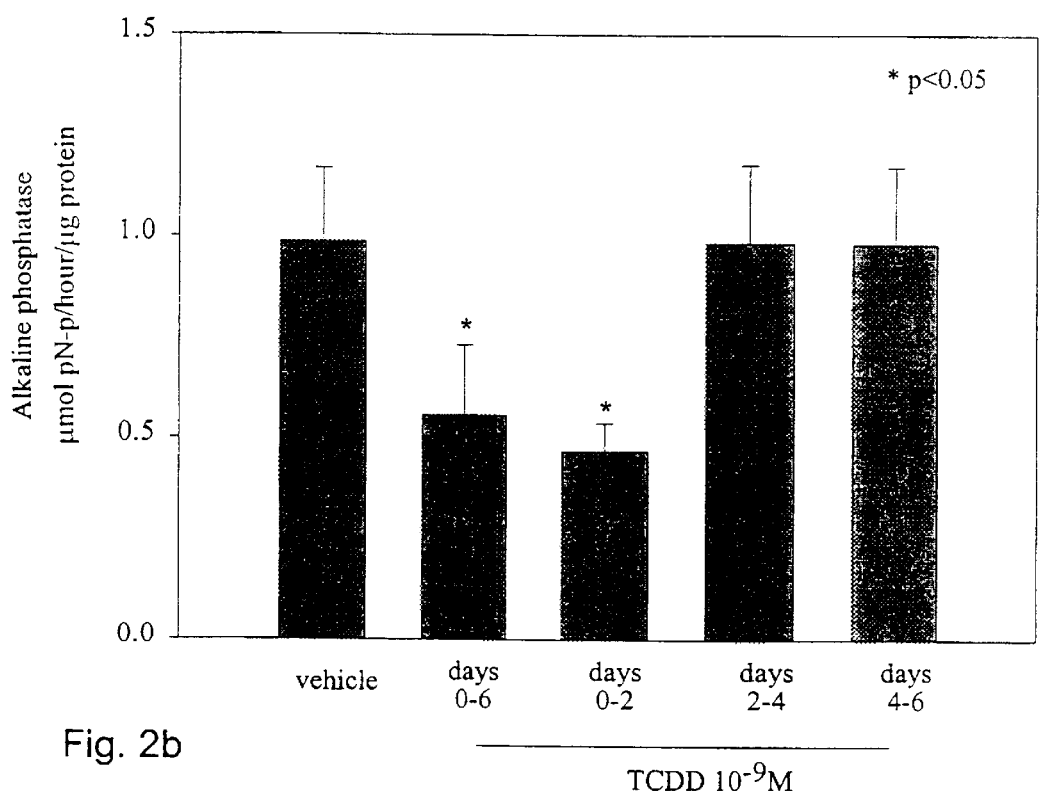
Figure 2C:
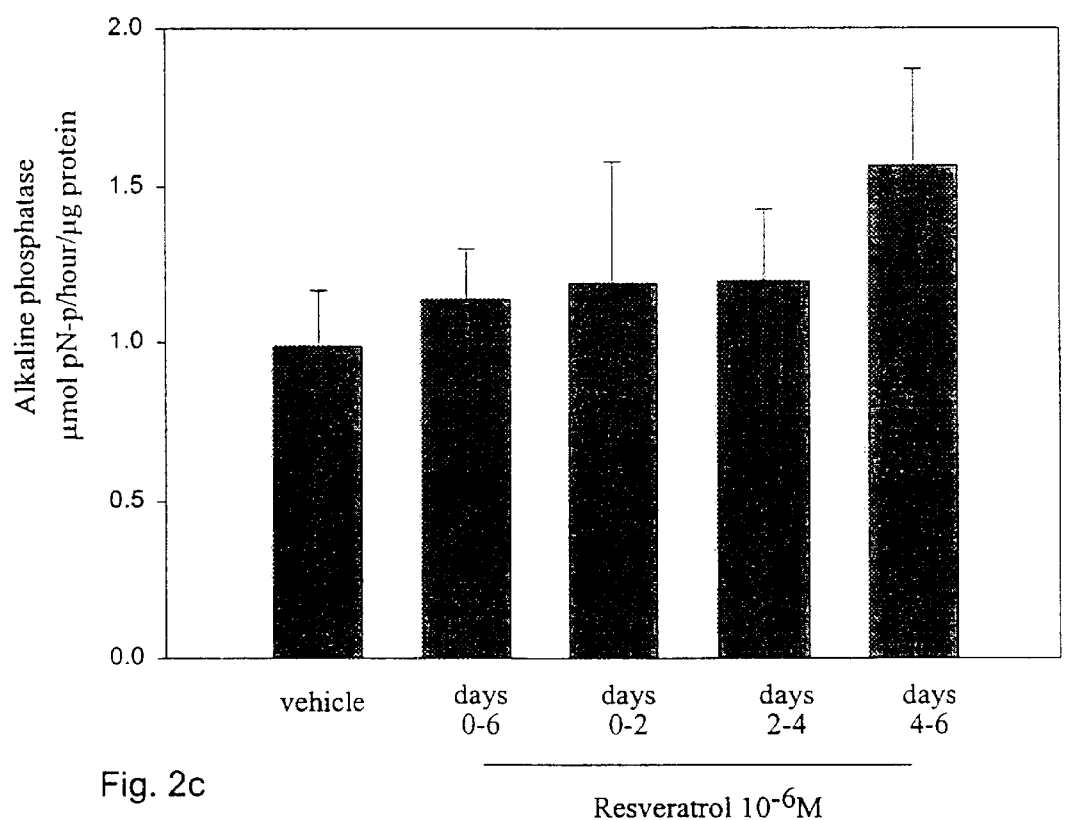
Figure 3:
FIG. 3 illustrates the agarose gel electrophoresis patterns for mRNA bands of the bone proteins, AP (alkaline phosphatase), BSP (bone sialoprotein), collagen type I and OPN (osteopontin) in CPO control cultures (C), cultures treated with TCDD (T), cultures treated with resveratrol (R) and cultures treated with TCDD and resveratrol (T+R)
Figure 3:
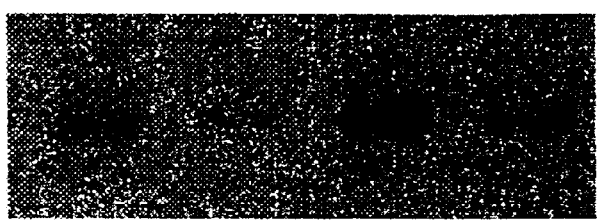
Figure 3:
Figure 3:
Figure 3:
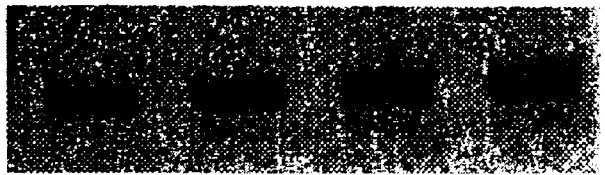
Figure 4:
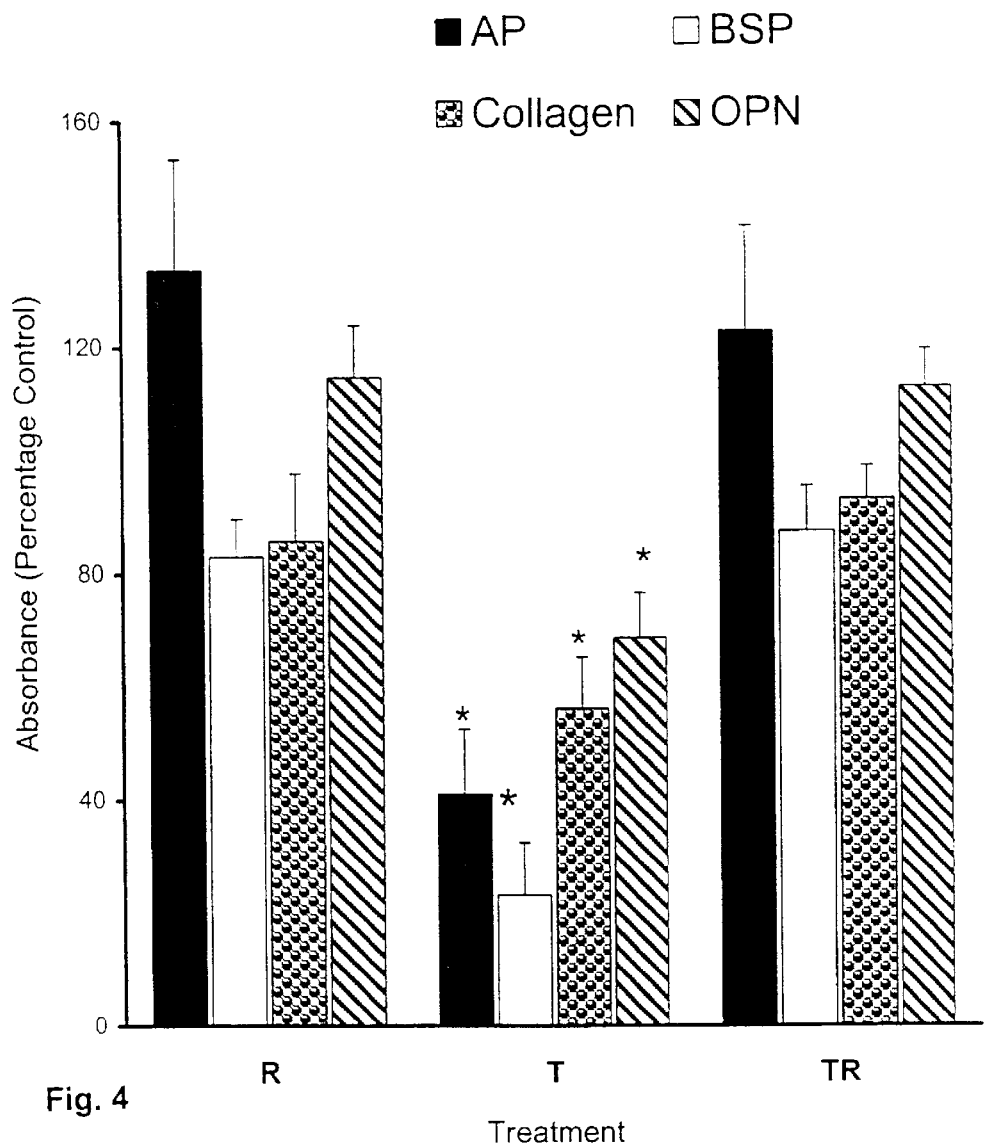
FIG. 4 is a bar graph illustrating the effect of resveratrol (R), TCDD (T) and resveratrol combined with TCDD (TR) on mRNA levels of the bone proteins, AP, BSP, collagen and OPN in the CPO model.

Cultures treated with $10^{-9}$M TCDD over a 6-day period showed 80% reduction in AP activity versus cultures with vehicle alone. Resveratrol, at doses of $10^{-5}$M, $10^{-6}$M and $10^{-7}$M partially prevented TCDD's inhibitory effects by increasing AP activity 2–4 fold in comparison to TCDD alone (FIG. 2a). Administration of $10^{-9}$M TCDD alone during days 2–4 or 4–6 did not significantly alter AP activity but administration during days 0–2 reduced AP activity by 53% similar to that of 6-day treatment ($p<0.05$ vs. vehicle) (FIG. 2b). No significant change in AP activity was noted when $10^{-6}$M resveratrol alone was added over days 0–6, days 0–2, days 2–4, or days 4–6 (FIG. 2c). As shown in FIGS. 3 & 4, message levels for AP were also reduced about 50% ($p<0.05$) in cultures treated with TCDD in comparison to control. In cultures treated with both TCDD and resveratrol, the mRNA levels were similar to control. In parallel with AP, mRNA levels for OPN were reduced by about 40% ($p<0.05$) in the presence of TCDD and restored in cultures treated with both TCDD and resveratrol. A similar profile was demonstrated for BSP in that there was about a 4-fold reduction in mRNA for BSP in the presence of TCDD ($p<0.05$) as shown in FIGS. 3 & 4. This inhibition was reversed completely with resveratrol. Interestingly, resveratrol alone appeared to partially down-regulate message for collagen and BSP but not other transcripts. β-actin bands were consistent in all groups (TCDD-treated, resveratrol-treated, TCDD- and resveratrol-treated and control) as would be expected for this "housekeeping gene".

Matrix Synthesis in the CPO

Figure 5:
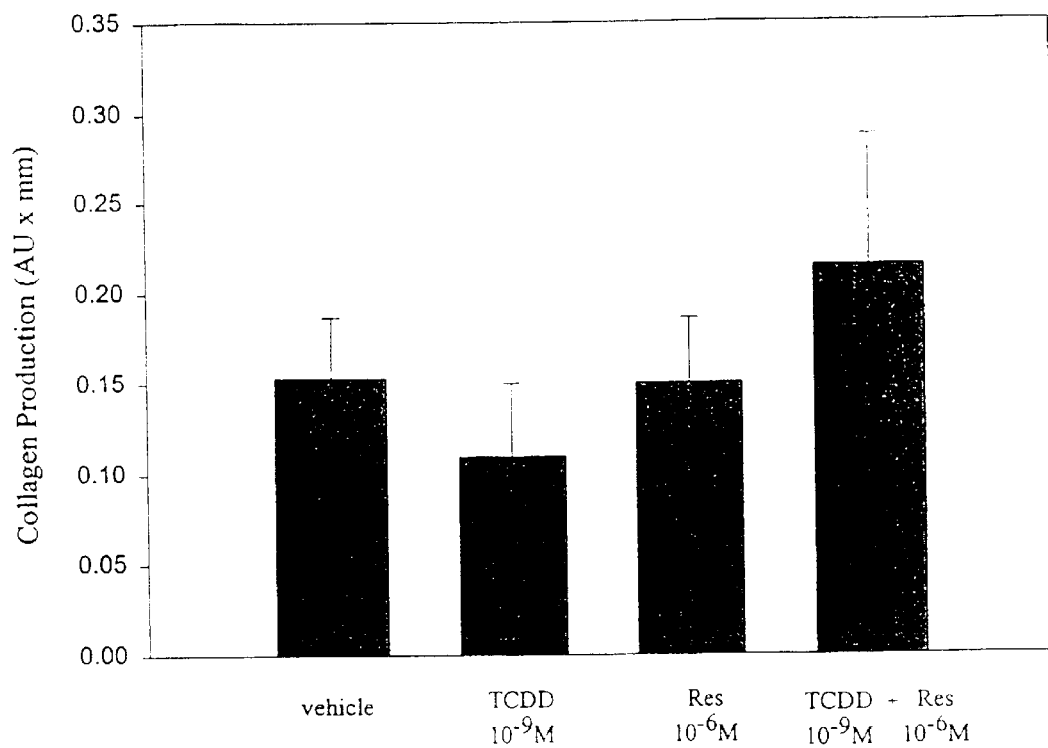
FIG. 5 is a bar graph illustrating the effect of TCDD, resveratrol and TCDD combined with resveratrol on collagen type I levels in the CPO model.

Newly synthesized collagen type I levels (reported as Absorbance Units (AU)×mm) were decreased by about 30% in the treatment groups receiving $10^{-9}$M TCDD alone ($p>0.05$), while $10^{-6}$M resveratrol alone had no effect compared to vehicle (FIG. 5). Co-treatment with TCDD and resveratrol increased the newly synthesized collagen type I level (FIG. 5a), but this was not significantly different from the collagen levels shown for cultures treated with TCDD alone. However, as shown in FIGS. 3 & 4, mRNA levels for type I collagen were reduced significantly (50%, $p<0.05$) in the presence of TCDD in comparison to control while cultures treated with both TCDD and resveratrol had identical levels of mRNA for Type I collagen.

Statistical Methods

All CPO experiments were carried out with 9 cultures per group (n=9) except for the mRNA extraction in which 12 cultures per group were utilized (n=12). The rat SBMC line experiments (described in Example 2 following) were carried out with 3 replicates per group (n=3) in all cases. In all experiments the results from each treatment group were compared only against the group which received vehicle-containing media (denoted as 'vehicle' in graphs). In the RT-PCR experiments, multiple comparisons between groups were performed using one-way ANOVA, and Student-Newman Keul's test for post-hoc analysis.

EXAMPLE 2

Effects of Resveratrol on Dioxin-Mediated Inhibition of Bone Cell Differentiation in the Rat Stromal Bone Marrow Cell line (RSBMC)

Cells for the rat SBMC model were obtained from Dr. Sandu Pitaru (Tel Aviv University, Israel) and maintained in $T_{25}$ tissue culture flasks (Sarstedt, Newton, N.C., USA) in a medium composed of αMEM+RNA+DNA+antibiotic supplemented with 10% fetal calf serum, 10 mM β-glycerophosphate, $10^{-8}$M dexamethasone, 50 µg/ml vitamin C and 3 ng/ml fibroblast growth factor. The media were changed every 48 hours and the cells subcultured when almost confluent (approximately every 72 hrs). Cells were grown for a period of 1–2 weeks to allow for formation of mineralized bone nodules.

SBMC cultures were assayed for AP activity using paranitrophenol-phosphate (pN-p) as the substrate as described above for CPO cultures. In some cases, AP activity was also measured using direct staining of SBMC cultures in 96 well plates as described previously (Tenenbaum et al., Anat Rec. 1995. 242(2):200–10). Mineralization in the SBMC cultures was determined using Alizarin Red staining in situ that was assessed with the Titertek spectrophotometer set at 525 nm.

Competitive Binding Assay for TCDD and Resveratrol

Four replicates were used in conducting the live whole cell (RSBMC) competition-binding assay to demonstrate specific receptor mediated uptake of radiolabeled TCDD. This technique has been described previously (Tenenbaum et al. Anat Rec. 1995. 242(2):200–10)) and demonstrates results that are comparable to more traditional binding assays relying on cytosol preparations. However, it should be pointed out that the binding curves produced using vital cell assays may be different than those produced using more standard cytosol binding assays. Thus, it is not possible to calculate Kd in these studies. However, this vital cell uptake/binding can be accomplished with far fewer cells than would otherwise be required to generate appropriate amounts of cytosol for more conventional assays. Notably, cytosol preparations are generally obtained from whole organs. Therefore, whereas mass cultures of cells would be required to obtain usable amounts of cytosol, we chose to rely on vital cell uptake studies despite the fact that "classic" competition/binding curves are not necessarily attainable with this approach. The need for preincubation (see below) may also alter competition kinetics in this type of binding assay. Cells were plated at a density of 10,000 per well in Titertek 96-well plates, and left overnight to attach in medium. The medium was removed by aspiration and the various concentrations of cold drug (TCDD, resveratrol) were prepared and added to the wells in a volume of 90 µl. Cells were preincubated with cold drug one hour prior to addition of radiolabeled TCDD (specific activity 33.4 Ci/mmol; Chemsyn Lab, Kansas) (pilot studies having shown that preincubation was required to detect competition). One set of wells was incubated without cold drug to determine total binding. $^3$H-TCDD (10,000 cpm/well in a volume of 10 µl) was added and incubated for 4 hours at room temperature. The media were aspirated and the cells washed 4× with 100 μl of PBS. 100 μl of 0.1N sulphuric acid was added and the cells were incubated at 37° C. overnight to break the cells open. 80 μl of the lysate was added to 5 ml of scintillation fluid and counted in a beta counter.

Results—SBMC Line

Alkaline Phosphatase

Figure 6:
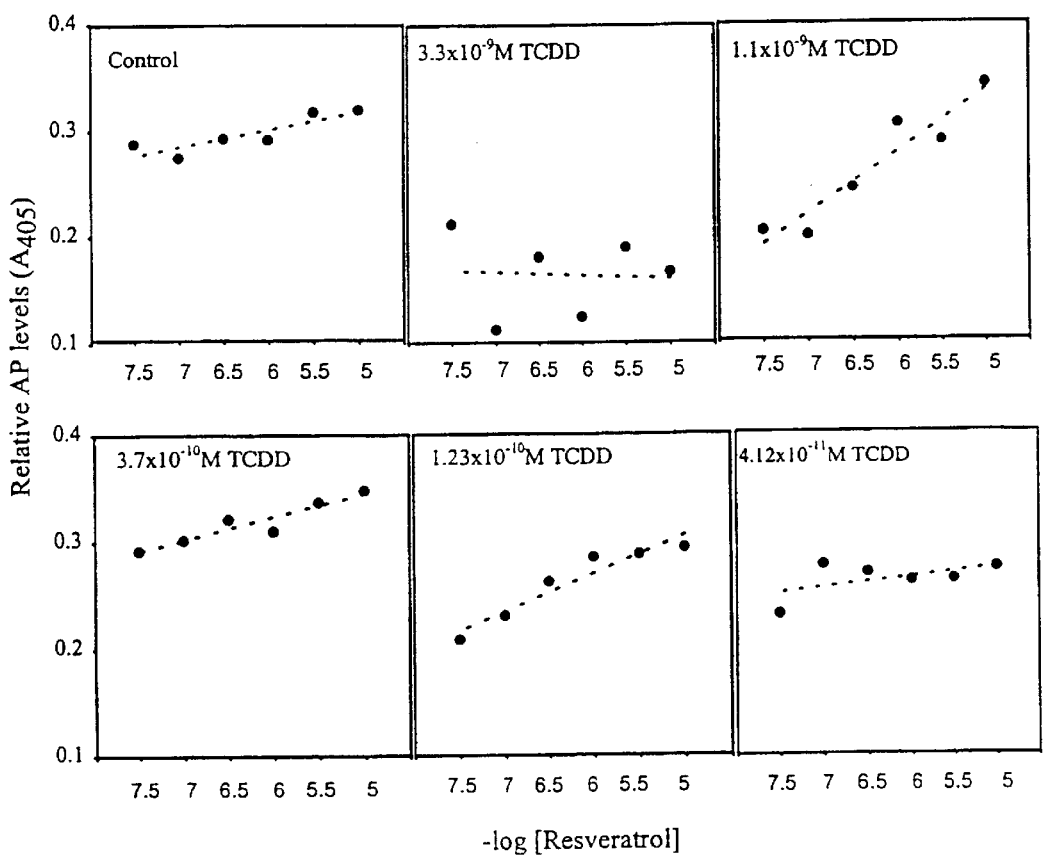
FIG. 6 illustrates the effect of various TCDD concentrations in the presence of increasing amounts of resveratrol on AP levels in the rat SBMC (stromal bone marrow cell) model.

As shown in FIG. 6, TCDD ($3.3 \times 10^{-9}$M and higher) induced a 33% reduction in AP activity versus control but this reduction was not reversed by administration of resveratrol at various concentrations. A 33% reduction in AP activity was also shown following treatment with a lower concentration of TCDD ($1.1 \times 10^{-9}$M). In this case, however, increasing concentrations of resveratrol ($4 \times 10^{-8}$M to $1 \times 10^{-5}$M) abrogated the effects of TCDD and brought AP activity back to, and even above that seen in control cultures. This pattern was repeated in the cultures receiving lower levels of TCDD. The initial reduction in AP activity due to TCDD was dose dependant ($3.3 \times 10^{-9}$M to $4.12 \times 10^{-11}$M). The abrogation of the effect of TCDD by increasing resveratrol concentrations was exhibited at each level of TCDD administration until a concentration of $4.12 \times 10^{-11}$M TCDD was reached. At this concentration, AP activity was not affected (i.e. similar to control) and the increasing concentration of resveratrol had no effect either. At several of the TCDD concentrations, the addition of the highest levels of resveratrol caused an increase in AP activity above that found in control.

Interestingly, this was also suggested in the CPO where mRNA for AP also demonstrated a tendency to be higher than control (see FIGS. 3 & 4).

Mineralization in the Rat SBMC Line

Figure 7:
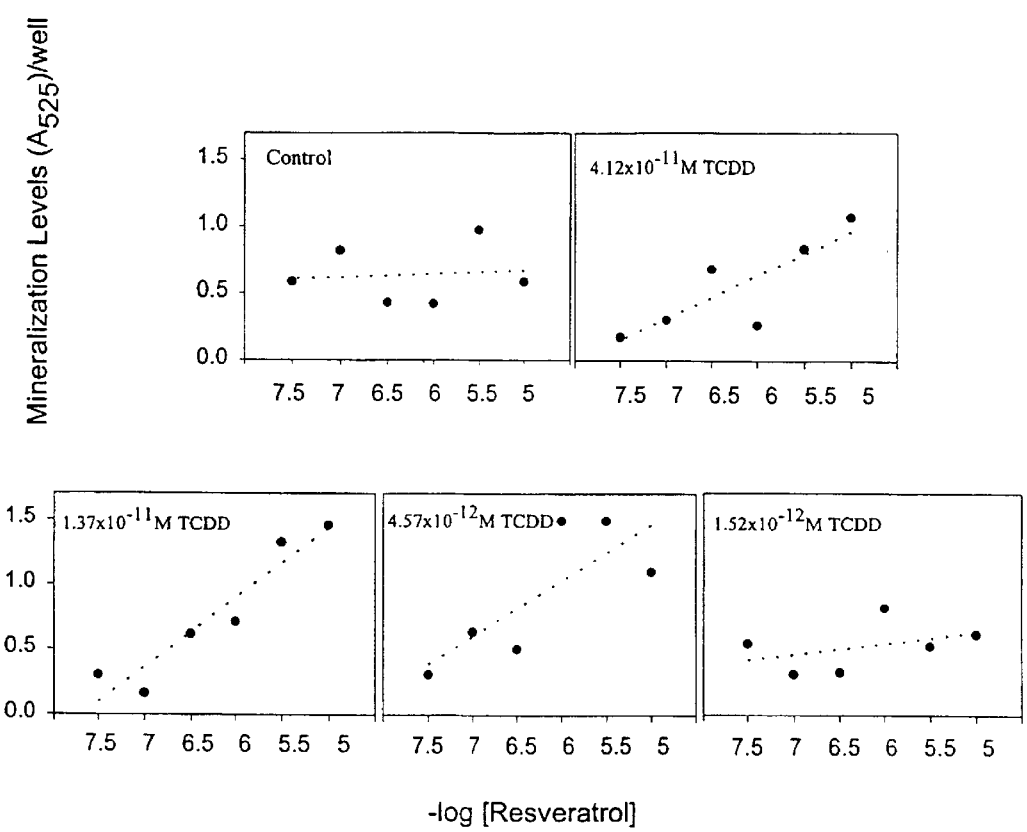
FIG. 7 illustrates the effect of various TCDD concentrations in the presence of increasing amounts of resveratrol on mineralization levels in the rat SBMC line.

There was a dose dependant reduction in mineralization (i.e. Alizarin Red Staining) in the presence of $4.12 \times 10^{-11}$M to $1.52 \times 10^{-12}$M TCDD (FIG. 7).

Mineralization was decreased by approximately 75% in the presence of TCDD which was attenuated by resveratrol. Interestingly, at the highest concentration of resveratrol, not only were TCDD effects attenuated but there appeared to be a 3-fold increase relative to control levels.

Specific Binding of TCDD and Resveratrol

Figure 8A:
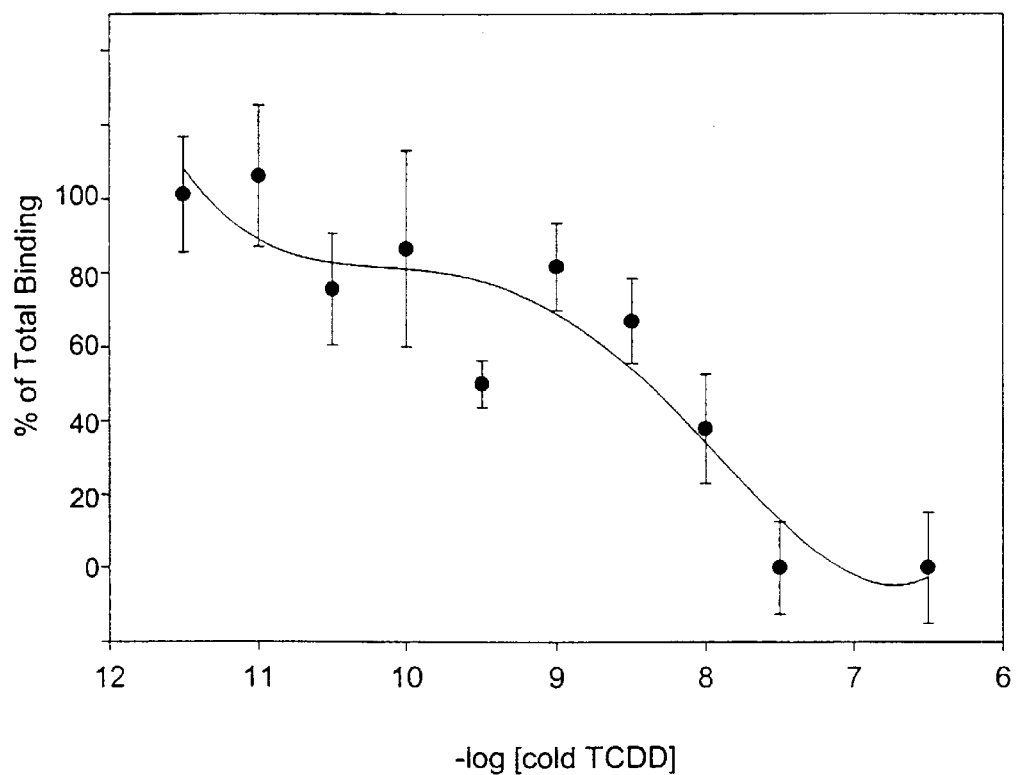
FIGS. 8A–B are graphs showing the results of live cell (SBMC) competitive uptake/binding assays between radiolabelled TCDD and unlabelled TCDD (A) and between radiolabelled TCDD and unlabelled resveratrol.
Figure 8B:
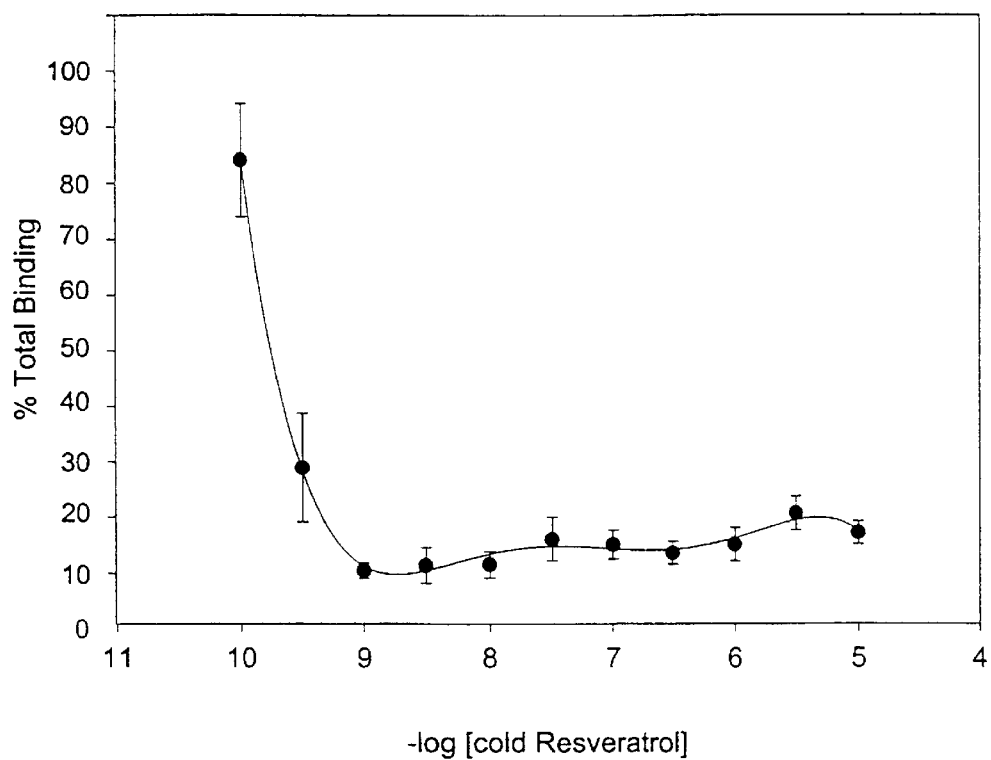

Increasing concentrations of TCDD effectively competed with $^3$H-TCDD for its cognate receptor and reduced binding to background levels at $3.3 \times 10^{-8}$M thus suggesting the existence of the AhR in SBMC cells despite the fact that "classic" competition curves were not demonstrated. Approximately 50% competition was achieved at $3.7 \times 10^{-9}$ M TCDD (FIG. 8a). Resveratrol competed with $^3$H-TCDD in a similar fashion. Resveratrol ($1.37 \times 10^{-9}$M) also reduced radiolabeled TCDD binding to background levels, while 50% competition occurred at $\sim 1.8 \times 10^{-10}$M resveratrol, a dose 20× lower than the dose of unlabeled TCDD required to produce this level of competition (FIG. 8b).

EXAMPLE 3

The Effects of Resveratrol on Dioxin-Mediated Inhibition of Bone Cell Differentiation in a Primary Rat Bone Marrow Cell (RBMC) Bone Formation System Rat bone marrow cells were derived from femoral bones removed from adult male Wistar rats as described previously (Maniatopoulos et al., Cell Tissue Res, 1988, 254(2): 317–330). These cells, grown in the presence of dexamethasone, vitamin C and b-glycerophosphate, differentiated into osteoblasts as shown by increases in APA and the production of mineralized bone nodules within 12–14 days. For the purposes of this investigation, we analyzed 10–16 day cultures for APA, as this was a reliable marker for osteoblastic differentiation in this system.

Figure 9:
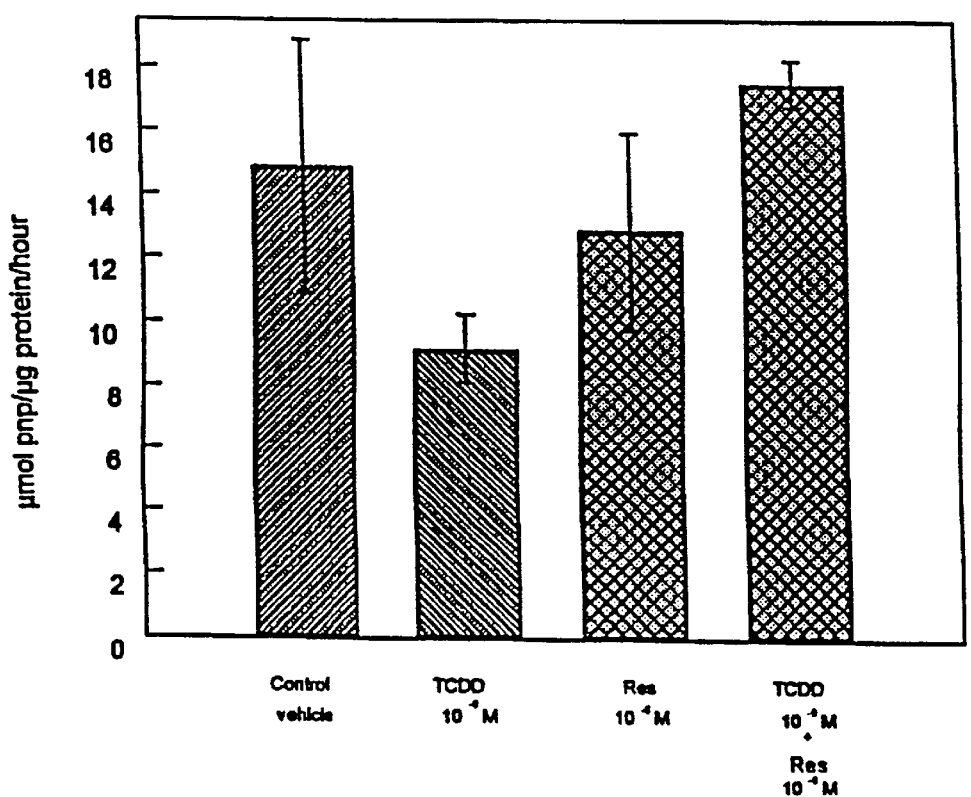
FIG. 9 is a bar graph illustrating the effect of TCDD on APA in rat bone marrow cells in the presence of resveratrol added either simultaneously with the TCDD or separately over days 4–10 of the culture.
Figure 10:
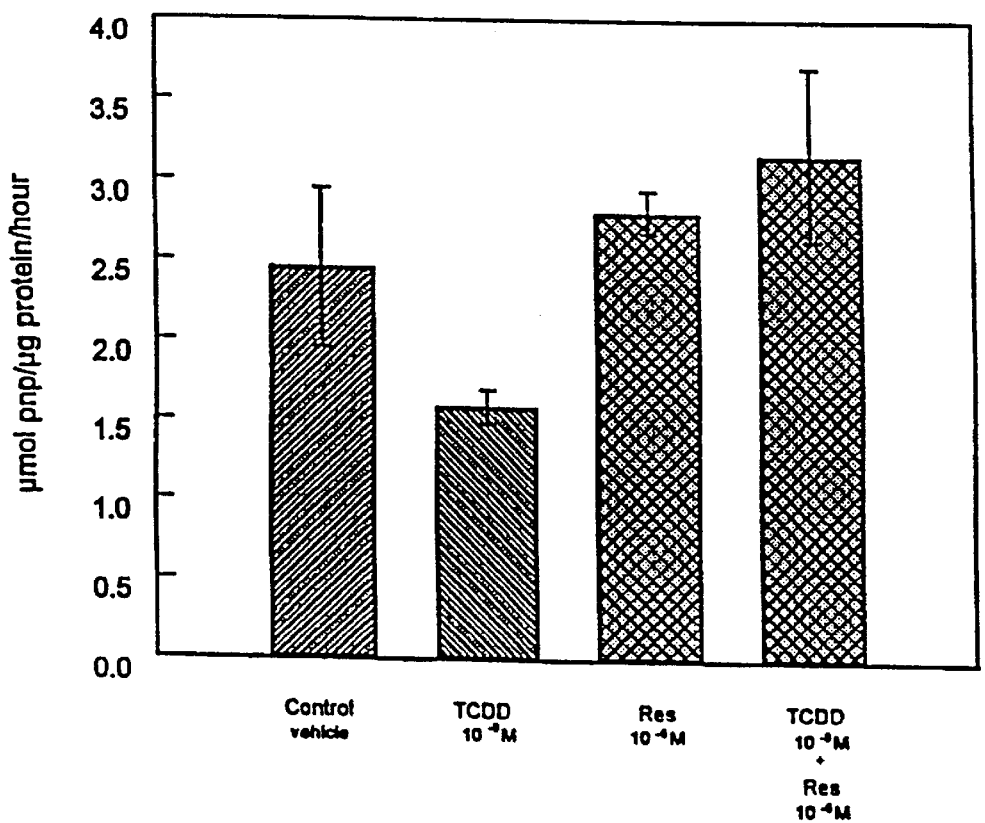
FIG. 10 is a bar graph as in FIG. 3 in which resveratrol is added either simultaneously with the TCDD or separately over days 10–16 of the culture.
Figure 11:
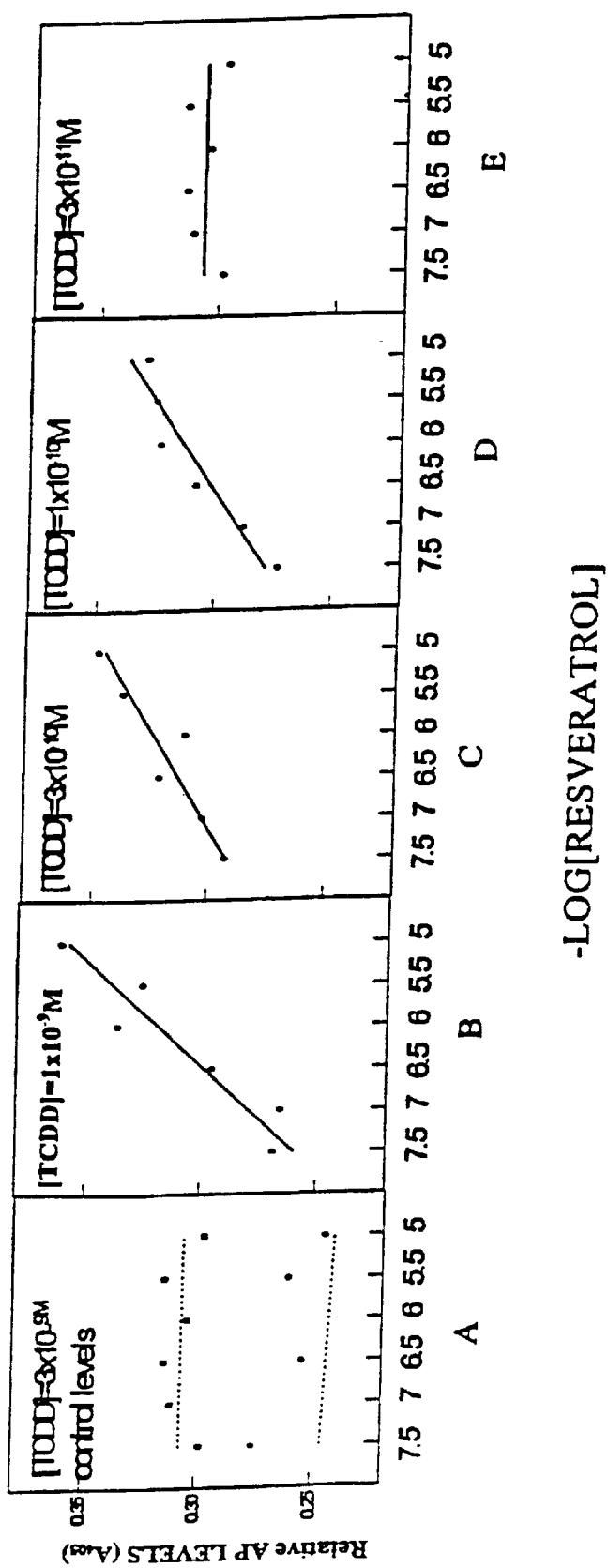
FIGS. 11A–E are a series of graphs illustrating the effects of increasing concentrations of resveratrol on APA activity in the presence of concentrations of TCDD which decrease in graphs A to E.

TCDD, when added to the cells at a concentration of $10^{-9}$ M in alcohol, inhibited osteodifferentiation compared to an alcohol-treated control, as measured by APA, by about 50% while resveratrol alone had no significant effects. Resveratrol, at a concentration of $10^{-6}$ molar in alcohol, completely abrogated the effects of TCDD when both agents were added together or singly between days 4–10 (FIG. 9). Similar results were observed when RBMC cultures were exposed to TCDD and resveratrol over days 10–16 (FIG. 10).

EXAMPLE 4

The Effects of Resveratrol on Dioxin-Mediated Inhibition of Bone Cell Differentiation in a Rat Bone Marrow Cell Line (RBMCL)

As shown in the CPO and the RBMC cultures, resveratrol was able to inhibit TCDD effects on osteoblastic differentiation in the RBMCL as assessed by APA. Interestingly, in the RBMCL, it appeared that a lower dose of TCDD was able to inhibit osteogenic differentiation, as seen in 6 day cultures, in comparison to that used in the CPO and RBMC. In any case, not only was resveratrol, at concentrations of from $4 \times 10^{-8}$M to $3 \times 10^{-5}$M, able to inhibit TCDD-mediated inhibition of osteoblastic differentiation but it appeared to stimulate APA in comparison to control (FIGS. 11A–E).

EXAMPLE 5

The Effects of Resveratrol on Benzo-a-pyrene-induced Bone Loss

In this experiment, the effects of the aryl hydrocarbon, benzo-a-pyrene (BaP) on the early events occurring during osteogenesis were determined. Ten-day old rat bone marrow cultures were treated with increasing concentrations of BaP. The effect of this treatment was monitored by APA as set out above. Alongside this experiment, an experiment in which rat bone marrow cultures were treated with BaP and resveratrol ($10^{-6}$M) was conducted.

Figure 12:
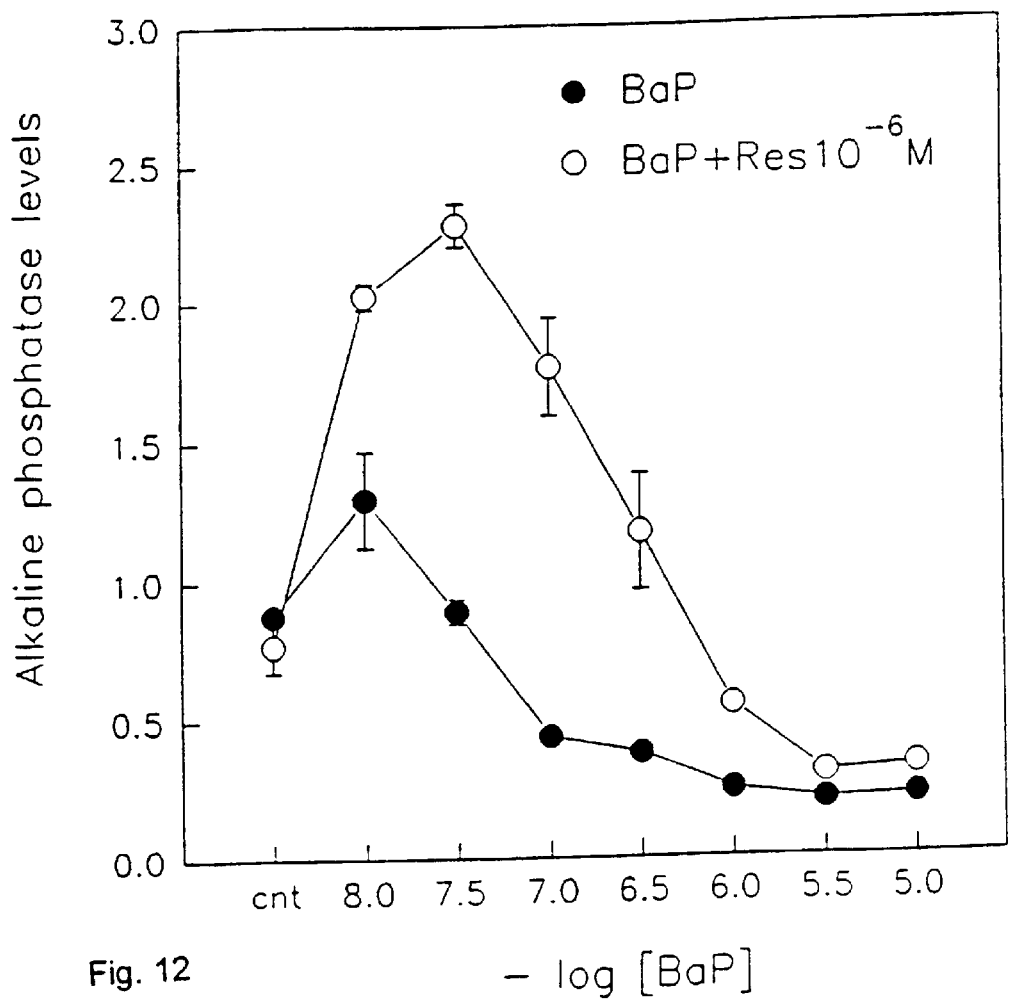
FIG. 12 is a graph illustrating the effect of BaP and resveratrol on APA in rat bone marrow cultures.
Figure 13:
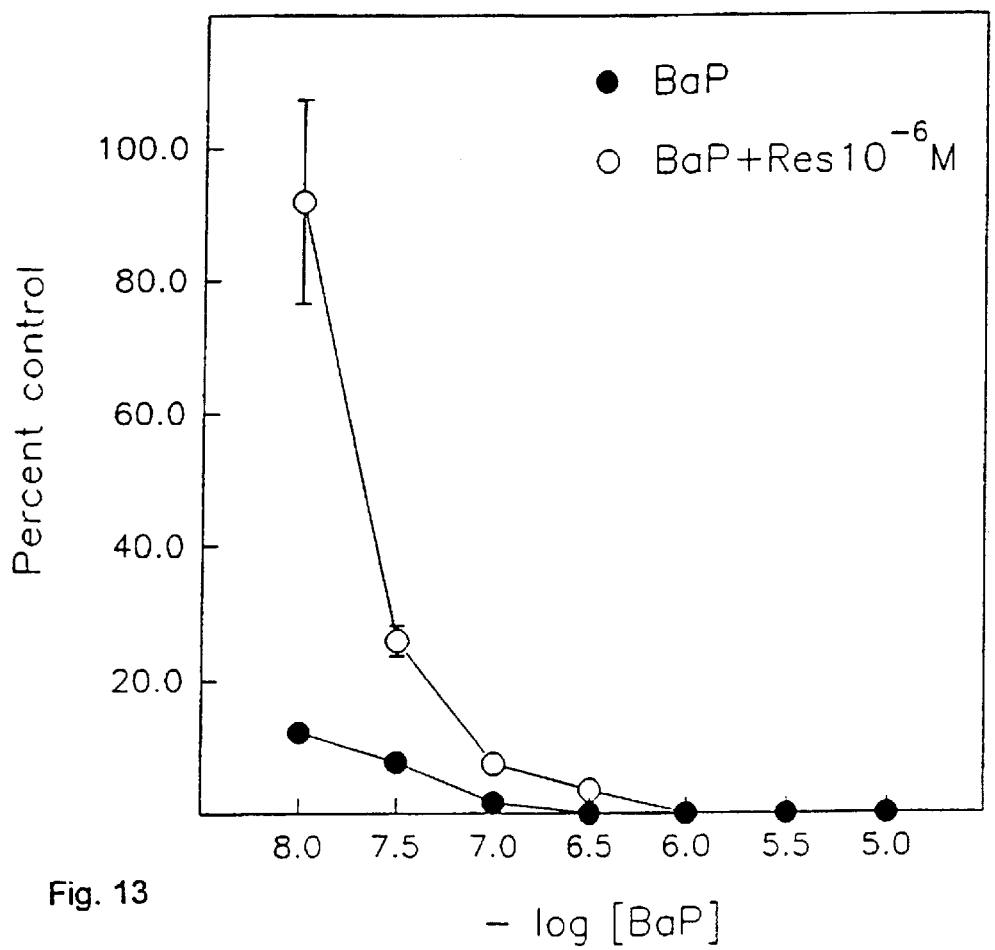
FIG. 13 is a graph illustrating the effect of adding resveratrol to BaP in reversing Bap inhibitory effects.

The results of these experiments are shown in FIGS. 12 and 13. BaP treatment resulted in an increased inhibition of alkaline phosphatase with increasing BaP concentration. When resveratrol was added with BaP to the cultures, there was not only a reversal of BaP's inhibitory effect, but an increase in alkaline phosphatase activity above that of the control activity (FIG. 12). BaP was shown to result in a decrease in mineral levels as BaP concentration was increased with as much as a 90% inhibition at $10^{-8}$M. Resveratrol and BaP together resulted in a complete reversal of the BaP effects at $10^{-8}$M with partial reversal at higher concentrations of BaP (FIG. 13).

Given the results of the foregoing experiments, aryl hydrocarbon receptor ligands (AhR) appear to have a profound inhibitory effect on osteogenic cell differentiation and mineralised bone formation in a variety of systems. Notably, these negative effects are either partially or completely abrogated by resveratrol depending on the relative doses of either agent used as well as the model systems used for testing. The effects of resveratrol are highly consistent with a receptor-mediated phenomenon. That these effects are demonstrated in different model systems and even in different species, supports the notion that these effects will be replicated in human model systems both in vitro and in vivo.

We claim:

1. A method for treating periodontal disease in a patient in need of such treatment, comprising administering to the oral cavity of the patient a therapeutically effective amount of a suitable aryl hydrocarbon receptor antagonist comprising resveratrol in a pharmaceutically acceptable carrier form which is selected from the group consisting of a rinse, a gel, a paste, a spray, a powder, a gum, a lozenge and a tablet.

2. A method as defined in claim 1, wherein the carrier form is administered at least once daily.

3. A method as defined in claim 1, wherein the carrier form is administered to the oral cavity of a patient for a period of about 30–60 seconds when said carrier form is in the form of a rinse.

4. A method as defined in claim 1, wherein the carrier form is administered to the oral cavity of a patient for a period of at least 1 minute when said carrier form is administered in the form of a paste or gel.

5. A method as defined in claim 1, wherein said carrier form comprises at least one additional active ingredient.

6. A method as defined in claim 5, wherein said additional active ingredient is selected from the group consisting of fluoride compounds, anti-caries agents, anti-bacterial agents, anti-tartar agents, anti-inflammatory agents, de-odourizers and stain removers.

7. A method as defined in claim 1, wherein said carrier form is in the form of a rinse or spray comprising a resveratrol dosage of from about 0.001–5 g/liter.

8. A method as defined in claim 1, wherein said carrier form is in the form of a paste or gel comprising a resveratrol dosage of from about 1–20 mg/g.

9. A method as defined in claim 1, wherein said carrier form is in the form of a gum comprising a resveratrol dosage of at least 0.2 mg/stick of gum.

10. A method as defined in claim 9 wherein said patient in need of such treatment being exposed to an environmental pollutant, or second hand tobacco smoke or is a smoker of tobacco products and the periodontal disease treated is caused by smoking or environmentally produced periodontal disease, and said resveratrol comprises micronized or dissolved resveratrol.

11. A method of treating bone loss and/or tooth attachment loss associated with periodontal disease in a patient in need of such treatment, said patient in need of such treatment being exposed to an environmental pollutant, or second hand tobacco smoke or is a smoker of tobacco products and the periodontal disease treated is caused by smoking or environmentally produced periodontal disease.

12. Use of the composition as claimed in claim 10, wherein said resveratrol comprises micronized resveratrol.

13. A method as defined in claim 11, wherein said composition is in the form of a topical formulation, and is administered to the oral cavity of said patient topically.

14. A method as claimed in claim 11, wherein said resveratrol comprises micronized resveratrol and said composition is in a form selected from the group consisting of a rinse, a gel, a paste, a spray, a powder, a tablet, a lozenge and a gum.

15. A method defined in claim 14, wherein said composition further includes an additional active ingredient selected from the group consisting of fluoride compounds, anti-caries agents, anti-bacterial agents, anti-tartar agents, anti-inflammatory agents, deodorizers and stain removers.

16. A method as claimed in claim 10, wherein said composition is in the form of a rinse or spray comprising a resveratrol dosage of from about 0.001–5 g/6 liter.

17. A method as claimed in claim 11, wherein said composition is in the form of a paste or gel comprising a resveratrol dosage of from about 1–20 mg/g.

18. A method as claimed in claim 10, wherein said composition is in the form of a gum comprising a resveratrol dosage of at least 0.2 mg/stick of gum.

19. A method as claimed in claim 11, wherein said composition is in the form of a rinse, gum or lozenge, and further comprising resveratrol dosage of about 1 milligram.

20. A method of manufacturing a medicament for the treatment of periodontal disease in individuals exposed to high levels of aryl hydrocarbons by micronizing or dissolving resveratrol, and admixing a therapeutically effective amount of said micronized or dissolved resveratrol with a pharmaceutically acceptable carrier.

21. A method as claimed in claim 20, wherein said resverstrol is micronized resveratrol.

22. A method of manufacture of a medicament for the inhibition of bone or tooth attachment loss associated with periodontal disease in smokers by micronizing or dissolving resveratrol, and admixing a therapeutically effective amount of said micronized or dissolved resveratrol with a pharmaceutically acceptable vehicle or excipient.

23. A method as claimed in claim 22, wherein said resveratrol is micronized resveratrol.

24. A method of manufacture of a medicament for the treatment of periodontal disease by micronizing or dissolving resveratrol, and admixing a therapeutically effective amount of said micronized or dissolved resveratrol with a pharmaceutically acceptable carrier form which is selected from the group consisting of a rinse, a gel, a paste, a spray, a powder, a gum, a lozenge and a tablet.

25. A method as defined in claim 1, wherein said periodontal disease is smoking induced periodontal disease.

* * * * *

SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence : pcr primer

<400> SEQUENCE: 1
gagcgggcac cggtacta                                                 18

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence : pcr primer

<400> SEQUENCE: 2
ctctagacac tgacatcctg ctc                                           23

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence : pcr primer

<400> SEQUENCE: 3
accgctgcaa caccacca                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence : pcr primer

<400> SEQUENCE: 4
tccccgcagg cttagtgt                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence : pcr primer

<400> SEQUENCE: 5
acccgaccct aagacaaa                                                 18

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence : pcr primer

<400> SEQUENCE: 6
tcggcgttgg ggcagt                                                   16

<210> SEQ ID NO 7
<211> LENGTH: 18

-continued

```
<212> TYPE: DNA
<213> ORGANISM: Artificial Sequence
<220> FEATURE:
<223> OTHER INFORMATION: Description of Artificial Sequence : pcr primer

<400> SEQUENCE: 7
aggccggggt gacagtgt                                                    18

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence : pcr primer

<400> SEQUENCE: 8
ccccgcaggc agcactc                                                     17
```